United States Patent [19]

Oftring et al.

[11] Patent Number: 4,670,591
[45] Date of Patent: Jun. 2, 1987

[54] PREPARATION OF N-α-ALKOXYETHYLFORMAMIDES

[75] Inventors: Alfred Oftring, Ludwigshafen; Erwin Hahn, Heidelberg; Rolf Fikentscher, Ludwigshafen, all of Fed. Rep. of Germany

[73] Assignee: BASF Aktiengesellschaft, Ludwigshafen, Fed. Rep. of Germany

[21] Appl. No.: 863,167

[22] Filed: May 14, 1986

[51] Int. Cl.$^4$ .................. C07C 103/44; C07C 103/38
[52] U.S. Cl. .................................................. 564/224
[58] Field of Search ....................................... 564/224

[56] References Cited

U.S. PATENT DOCUMENTS

| | | | |
|---|---|---|---|
| 2,422,598 | 6/1947 | Stiller | 564/224 X |
| 3,531,471 | 9/1970 | Hartwimmer et al. | 564/224 X |
| 4,529,822 | 7/1985 | Duranleau et al. | 564/224 X |

Primary Examiner—Paul F. Shaver
Attorney, Agent, or Firm—Oblon, Fisher, Spivak, McClelland & Maier

[57] ABSTRACT

N-α-alkoxyethylformamides of the formula

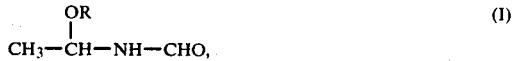

where R is $C_1$–$C_{18}$-alkyl, are prepared by reacting a vinyl ether of the formula

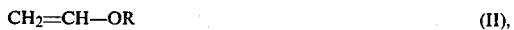

where R has the meaning stated in the formula I, with formamide in the presence of an acidic or basic catalyst at from −10° to 150° C.

8 Claims, No Drawings

PREPARATION OF N-α-ALKOXYETHYLFORMAMIDES

European Pat. No. 19,226 discloses a process for the preparation of N-α-alkoxyethylcarboxamides, in which an N-ethylcarboxamide is anodically oxyalkylated with an alcohol in the presence of a conductive salt in an electrolysis cell. The electrochemical process appears to be very expensive from the point of view of both the procedure and the costs of the starting materials.

It is an object of the present invention to provide another, more advantageous process for the preparation of N-α-alkoxyethylformamides.

We have found that this object is achieved, according to the invention, if a vinyl ether of the formula

$$CH_2=CH-OR \quad (II)$$

where R is $C_1$–$C_{18}$-alkyl, is reacted with formamide in the presence of an acidic or basic catalyst at from $-10°$ to $150°$ C.

Compounds of the formula II, where R is $C_1$–$C_4$-alkyl, are preferably used, ie. vinyl methyl ether, vinyl ethyl ether, vinyl n-propyl ether, vinyl isopropyl ether, vinyl n-butyl ether, vinyl isobutyl ether and vinyl tert-butyl ether.

Other suitable vinyl alkyl ethers for the process according to the invention are those in which alkyl is of not more than 18 carbon atoms, eg. vinyl hexyl ether, vinyl 2-ethylhexyl ether, vinyl isooctyl ether, vinyl nonyl ether, vinyl dodecyl ether, vinyl palmityl ether and vinyl stearyl ether.

The vinyl ethers of the formula II are reacted with formamide according to the equation

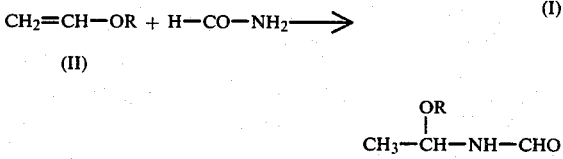

in the presence of an acidic or basic catalyst at from $-10°$ to $150°$ C., preferably from $0°$ to $70°$ C. In formulae I and II, R is $C_1$–$C_{18}$-alkyl. The compounds of the formula II are reacted with formamide in a molar ratio of from 20:1 to 1:2, preferably from 3:1 to 1:1. Excess vinyl alkyl ether acts as a diluent.

The reaction can, if required, also be carried out in a polar solvent which is inert under the reaction conditions. Examples of suitable solvents are diethyl ether, tetrahydrofuran, dioxane, dimethylformamide, dimethyl glycol ether, diethyl glycol ether, methylglycol, ethylglycol, polyethylene glycols which contain from 2 to 15 ethylene oxide units, propylene glycol, polypropylene glycols which are liquid at room temperature and contain from 2 to 15 propylene oxide units, ethylene oxide/propylene oxide block copolymers which are liquid at $20°$ C., $C_1$–$C_4$-alcohols, such as methanol, ethanol, isopropanol, n-propanol, n-butanol, isobutanol and tert-butanol, and acetonitrile. If the reaction is carried out in an inert solvent, up to 1000, preferably from 10 to 200, parts by weight of an inert solvent or a mixture of several inert solvents is used per 100 parts by weight of the mixture of vinyl ether and formamide. The solvent used in each case should be matched with the catalyst, ie. the solvent must be inert under the reaction conditions.

The reaction of the two reactants described above will occur only in the presence of an acidic or basic catalyst. Suitable acidic catalysts are strong acids whose $pK_a$ is not more than 2, eg. sulfuric acid, amidosulfonic acid, aliphatic and aromatic sulfonic acids, such as trifluoromethanesulfonic acid, methanesulfonic acid, benzenesulfonic acid or p-toluenesulfonic acid, and Lewis acids, eg. boron trifluoride diethyl etherate, tin(IV) chloride, $AlBr_3$, $FeBr_2$, $FeCl_3$, $ZnCl_2$, $AlCl_3$, $TiCl_4$ and $CuCl_2$. Mixtures of different acids or mixtures of sulfuric acid and a Lewis acid, eg. $BF_3$ etherate, may also be used.

Examples of suitable basic catalysts are tertiary amines, such as triethylamine, triethanolamine, dimethylhexylamine, pyridine, quinoline, quinolidine, 1,4-diazabicyclo[2,2,2]octane and pyrrocoline. It is of course also possible to use mixtures of different basic catalyts.

The acidic or basic catalysts are used in the reaction in an amount of from 0.1 to 10, preferably from 0.5 to 5, % by weight, based on the vinyl ether and formamide used. Preferably, acidic catalysts are used, and the reaction is carried out at from $0°$ to $70°$ C. Particularly useful compounds of the formula II are vinyl methyl ether and vinyl ethyl ether, which are reacted with formamide in a molar ratio of from 3:1 to 1:1 in the presence of from 0.5 to 5% by weight of boron trifluoride diethyl etherate as an acidic catalyst. The reactions are preferably effected in the absence of oxygen, in an inert gas atmosphere. The inert gas principally used is nitrogen. The reaction is preferably carried out in an anhydrous medium or substantially in the absence of water, although up to about 1% by weight, based on vinyl ether and formamide, of water may be present in the reaction mixture. The reaction may be carried out under atmospheric pressure, superatmospheric pressure, eg. up to 100 bar, or reduced pressure.

When the reaction is complete, the reaction mixture is purified. To remove the catalyst used, neutralization is effected. If an acidic catalyst has been used, for the sake of simplicity sodium carbonate is added to the reaction mixture, excess sodium carbonate and the salt formed in each case in the neutralization are separated off, for example by filtration, and the filtrate is distilled.

The resulting N-α-alkoxyethylformamide of the formula I may be converted to N-vinylformamide by pyrolysis with elimination of R—OH, where R has the meaning stated in formula I. N-Vinylformamide is a useful monomer, which can be converted, for example by homopolymerization followed by partial hydrolysis, to highly effective cationic flocculents as well as retention agents, and drainage aids in papermaking. The pyrolysis of the compounds of the formula II is carried out under atmospheric pressure or, preferably, under reduced pressure, eg. from 5 to 500, in particular from 10 to 200, mbar, at from $200°$ to $650°$ C., preferably from $300°$ to $550°$ C., and may be effected over a solid catalyst, eg. $SiO_2$, alumina, $Al_2O_3$, marble, iron, copper, MgO or ZnO, or a mixture of suitable solids. The catalysts may be in the form of rings, spheres, extrudates or hollow bodies.

In the Examples, parts are by weight.

EXAMPLE 1

A solution of 58 g (1 mole) of vinyl methyl ether in 40 g of tetrahydrofuran is initially taken in a flask and cooled to 5° C. Thereafter, a solution of 45 g (1 mole) of formamide, 1.5 g (0.01 mole) of boron trifluoride diethyl etherate and 30 g of tetrahydrofuran is added in the course of 6 hours at a reaction temperature of from 0° to 5° C. while stirring vigorously. The reaction is carried out in the absence of oxygen, in a nitrogen atmosphere. The reaction mixture is then stirred for 12 hours at room temperature, 5 g of solid sodium carbonate are added, the mixture is filtered, and the tetrahydrofuran used as a solvent and other volatile constituents are distilled off at 25° C. under reduced pressure from a waterpump. An oily residue remains, which is then fractionally distilled over a 30 cm long column. 65 g (63% of theory) of N-α-methoxyethylformamide are obtained in the form of a colorless liquid of boiling point 47°–49° C. under 0.2 mbar.

EXAMPLE 2

A mixture of 45 g (1 mole) of formamide and 1.5 g (0.01 mole) of trifluoromethanesulfonic acid is added dropwise, at from 0° to 5° C. in the course of 6 hours, to a solution, at 5° C., of 72 g (1.2 moles) of vinyl methyl ether in 70 g of acetonitrile, with vigorous stirring and in the absence of oxygen, in a nitrogen atmosphere. Thereafter, the reaction mixture is stirred for one hour at 10° C. and then for 20 hours at 20° C., and is neutralized by adding n-tributylamine. Volatile constituents of the reaction mixture are distilled off under reduced pressure from a waterpump, the mixture being heated to no higher than 25° C. The oil which remains is then fractionally distilled off to give 57 g (55% of theory, based on formamide) of N-α-methoxyethylformamide of boiling point 59°–62° C. under 0.5 mbar.

EXAMPLE 3

Example 2 is repeated, except that, instead of trifluoromethanesulfonic acid, 1.6 g (0.01 mole) of p-toluenesulphonic acid is used as the acidic catalyst. N-α-Methoxyethylformamide is obtained in a yield of 45% based on formamide.

EXAMPLE 4

72 g (1 mole) of vinyl ethyl ether are initially taken in a three-necked flask equipped with a thermometer, a reflux condenser and a dropping funnel, and are heated to 35° C. A solution of 22.5 g (0.5 mole) of formamide and 3 g (0.018 mole) of p-toluenesulfonic acid is added in the course of 5 hours at this temperature, while mixing vigorously. The reaction mixture is then stirred for a further 2 hours at 35° C., 5 g of sodium carbonate are added, the salts are filtered off and the solution is evaporated down under reduced pressure from a waterpump. The oily residue which remains is then fractionally distilled over a 30 cm long column to give 46 g (79% of theory, based on formamide) of N-α-ethoxyethylformamide of boiling point 49°–52° C. under 0.1 mbar.

EXAMPLE 5

A mixture of 45 g (1 mole) of formamide and 3 g (0.011 mole) of tin(IV) chloride is added dropwise, at 35° C. in the course of 7 hours, to 72 g (1 mole) of vinyl ethyl ether, with vigorous stirring and in the absence of oxygen, in a nitrogen atmosphere. When the mixture of formamide and the catalyst has been added, the reaction mixture is stirred for a further 5 hours at 40° C., after which volatile constituents are distilled off under reduced pressure from a waterpump, the residue is taken up in 300 ml of chloroform and the resulting solution is washed with twice 150 ml of a saturated sodium chloride solution. The organic phase is then dried over sodium sulfate, the solvent is distilled off and the residue is fractionally distilled under 0.1 mbar to give N-α-ethoxyethylformamide in a yield of 53% of theory, based on the formamide used.

EXAMPLE 6

150 g (2.5 moles) of vinyl methyl ether in 100 g of tetrahydrofuran are initially taken, at 5° C., in a three-necked flask equipped with a thermometer, a reflux condenser and a dropping funnel. A mixture of 90 g (2 moles) of formamide, 3.6 g (0.045 mole) of absolute pyridine and 80 g of tetrahydrofuran is added dropwise at this temperature in the course of 7 hours under a nitrogen atmosphere. The reaction mixture is then left at 5° C. for 1 hour, after which stirring is continued for a further 48 hours at 20° C.

The pH is then brought to 7–6.5 by adding glacial acetic acid, and volatile constituents are distilled off under reduced pressure from a waterpump at up to 25° C.

Fractional distillation under reduced pressure gives 84 g (41% of theory, based on formamide) of N-α-methoxyethylformamide.

We claim:

1. A process for the preparation of a N-α-alkoxyethylformamide of the formula

where R is $C_1$–$C_{18}$-alkyl, wherein a vinyl ether of the formula

where R is $C_1$–$C_{18}$-alkyl, is reacted with formamide in the presence of an acidic or basic catalyst at from −10° to 150° C.

2. A process as claimed in claim 1, wherein a compound of the formula II is reacted with formamide in a molar ratio of from 20:1 to 1:2.

3. A process as claimed in claim 1 or 2, wherein the reaction is carried out in the presence of from 0.1 to 10% by weight, based on vinyl ether and formamide, of an acidic or basic catalyst.

4. A process as claimed in claim 1, wherein the reaction is carried out in the presence of an acidic catalyst at from 0° to 70° C.

5. A process as claimed in claim 1, wherein sulfuric acid, amidosulfonic acid, an aliphatic or aromatic sulfonic acid and/or a Lewis acid are used as acidic catalysts.

6. A process as claimed in claim 1, wherein a tertiary amine is used as the basic catalyst.

7. A process as claimed in claim 1, wherein a vinyl ether of the formula II, where R is $C_1$–$C_4$-alkyl, is used.

8. A process as claimed in claim 1, wherein vinyl methyl ether is reacted with formamide in a molar ratio of from 1:3 to 1:1 in the presence of from 0.5 to 5% by weight of boron trifluoride diethyl etherate, p-toluenesulfonic acid, trifluoromethanesulfonic acid or tin tetrachloride as an acidic catalyst.

* * * * *

UNITED STATES PATENT AND TRADEMARK OFFICE
CERTIFICATE OF CORRECTION

PATENT NO. : 4,670,591

DATED : June 2, 1987

INVENTOR(S) : Oftring, et al.

It is certified that error appears in the above-identified patent and that said Letters Patent is hereby corrected as shown below:

On the title page insert:

-- Foreign Application Priority Data

June 11, 1985 [DE] Fed. Rep. of Germany....
................3520829--

Signed and Sealed this

Tenth Day of November, 1987

Attest:

DONALD J. QUIGG

Attesting Officer

Commissioner of Patents and Trademarks